United States Patent
Hu et al.

(10) Patent No.: US 10,839,936 B2
(45) Date of Patent: Nov. 17, 2020

(54) EVIDENCE BOOSTING IN RATIONAL DRUG DESIGN AND INDICATION EXPANSION BY LEVERAGING DISEASE ASSOCIATION

(71) Applicant: International Business Machines Corporation, Armonk, NY (US)

(72) Inventors: Jianying Hu, Bronx, NY (US); Zhaonan Sun, Elmsford, NY (US); Fei Wang, Farmington, CT (US); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1364 days.

(21) Appl. No.: 14/929,995

(22) Filed: Nov. 2, 2015

(65) Prior Publication Data
US 2017/0124469 A1   May 4, 2017

(51) Int. Cl.
*G16B 5/00*   (2019.01)
*G16C 20/50*   (2019.01)

(52) U.S. Cl.
CPC ............... *G16B 5/00* (2019.02); *G16C 20/50* (2019.02)

(58) Field of Classification Search
None
See application file for complete search history.

(56) References Cited

U.S. PATENT DOCUMENTS

| | | |
|---|---|---|
| 2014/0162900 A1 | 6/2014 | Hellerstein |
| 2014/0193517 A1 | 7/2014 | Agarwal et al. |
| 2015/0006439 A1 | 1/2015 | Cao et al. |
| 2015/0133390 A1 | 5/2015 | Khatri et al. |
| 2015/0134266 A1 | 5/2015 | Cardozo et al. |

OTHER PUBLICATIONS

Sirota et al. "Discovery and preclinical validation of drug indications using compendia of public gene expression data." Science translational medicine 3.96 (2011): 96ra77-96ra77.
Gottlieb et al. "PREDICT: a method for inferring novel drug indications with application to personalized medicine." Molecular systems biology 7.1 (2011): 496.
Zhao et al., . "A co-module approach for elucidating drug-disease associations and revealing their molecular basis." Bioinformatics 28.7 (2012): 955-961.
Mathur et al., "Drug repositioning using disease associated biological processes and network analysis of drug targets." AMIA Annual Symposium Proceedings. vol. 2011. American Medical Informatics Association, 2011.
Yu et al. "Inferring drug-disease associations based on known protein complexes." BMC Medical Genomics 8.Suppl 2(2015): S2.
Chiang AP, Butte AJ. Systematic evaluation of drug-disease relationships to identify leads for novel drug uses. Clin Pharmacol Ther 2009; 86(5):507-510.
Luo H, Chen J, Shi L, Mikailov M, Zhu H, Wang K, He L, Yang L. DRAR-CPI: a server for identifying drug repositioning potential and adverse drug reactions via the chemical-protein interactome. Nucleic Acids Res 2011; 39 (Web Server issue):W492-W498.
Wang F, Zhang P, Cao N, Hu J, Sorrentino R. Exploring the associations between drug side-effects and therapeutic indications. Journal of Biomedical Informatics 2014; 51:15-23.
Zhang Y, Yeung DY. A convex formulation for learning task relationships in multi-task learning. In Proceedings of theTwenty-Sixth Conference on Uncertainty in Artificial Intelligence (UAI) 2010; 433-442.
Wang X, Wang F, Hu J. A multi-task learning framework for joint disease risk prediction and comorbidity discovery . Nucleic Acids Res 2011In 22nd International Conference on Pattern Recognition (ICPR) 2014; 220-225.
Gong P, Ye J, Zhang C. Robust multi-task feature learning. n Proceedings of the 18th ACM SIGKDD International Conference on Knowledge Discovery and Data Mining (KDD) 2012; 895-903.
Goncalves AR, Das P, Chatterjee S, Sivakumar V, Zuben FJV, Banerjee A. Multi-task sparse structure learning. In 23rd ACM International Conference on Information and Knowledge Management (CIKM) 2014; 451-460.
Zhou J, Chen J, Ye J. Clustered Multi-Task Learning Via Alternating Structure Optimization. Advances in Neural Information Processing Systems (NIPS) 2011; 702-710.
Kim S, Xing E. Tree-guided group lasso for multi-task regression with structured sparsity. In Proceedings of the 27th International Conference on Machine Learning 2010; 543-550.
Jalali A, Sanghavi S, Ruan C, Ravikumar PK. A dirty model for multi-task learning. Advances in Neural Information Processing Systems (NIPS) 2010; 964-972.

*Primary Examiner* — G Steven Vanni
(74) *Attorney, Agent, or Firm* — Kristofer L. Haggerty

(57) ABSTRACT

An embodiment of the invention receives input including a list of drugs, drug characteristics of each drug, and known drug-disease associations including a disease and a drug having a threshold efficacy for treating the disease. For each drug in the list of drugs, a processor predicts whether the drug meets a threshold efficacy for treating a first disease based on the drug characteristics and the drug-disease associations. For each drug in the list of drugs, the processor predicts whether the drug meets a threshold efficacy for treating a second disease based on the drug characteristics and the predicting of whether the drug meets the threshold efficacy for treating the first disease. Output is generated output based on the predictions, the output including an identified drug-disease association, an identified disease-disease association, an identified chemical fingerprint for the first disease, and an identified chemical fingerprint for the second disease.

20 Claims, 13 Drawing Sheets

Key fingerprints for acute pulmonary heart disease (415)

| Rank | Relevance score | Fingerprint ID | Fingerprint definition |
|---|---|---|---|
| 1 | 0.3247712048 | SUB199 | >= 4 any ring size 6 |
| 2 | 0.251260391 | SUB124 | >= 2 saturated or aromatic nitrogen-containing ring size 3 |
| 3 | 0.195194069 | SUB122 | >= 2 any ring size 3 |
| 4 | 0.174516616 | SUB151 | >= 2 saturated or aromatic carbon-only ring size 5 |
| 5 | 0.169634787 | SUB209 | >= 5 saturated or aromatic heteroatom-containing ring size 6 |

FIG. 3

Key fingerprints for Schizophrenia (295)

| Rank | Relevance Score | Fingerprint ID | Fingerprint definition |
|---|---|---|---|
| 1 | 0.553765151 | SUB149 | >= 1 unsaturated non-aromatic heteroatom-containing ring size 5 |
| 2 | 0.427310885 | SUB148 | >= 1 unsaturated non-aromatic nitrogen-containing ring size 5 |
| 3 | 0.384328565 | SUB151 | >= 2 saturated or aromatic carbon-only ring size 5 |
| 4 | 0.351089809 | SUB152 | >= 2 saturated or aromatic nitrogen-containing ring size 5 |
| 5 | 0.346201986 | SUB201 | >= 4 saturated or aromatic nitrogen-containing ring size 6 |

FIG. 4

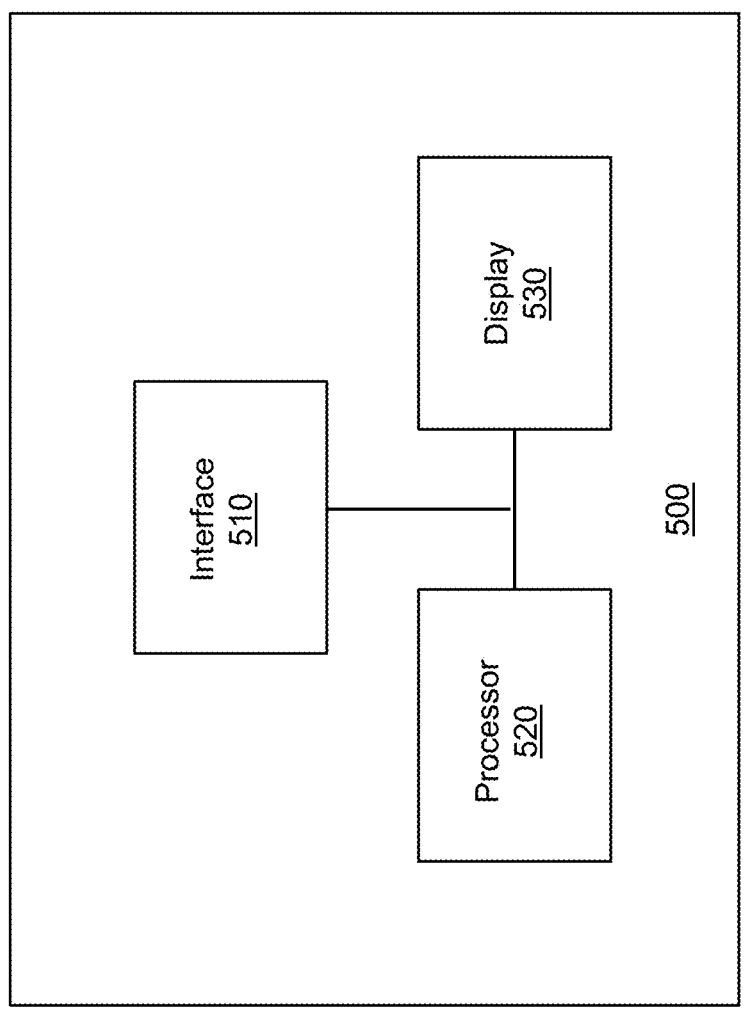

FIG. 7(b) Multi-task learning

FIG. 7(a) Single-task learning

EVIDENCE BOOSTING IN RATIONAL DRUG DESIGN AND INDICATION EXPANSION BY LEVERAGING DISEASE ASSOCIATION

BACKGROUND

The present invention relates to systems, methods, and computer program products for evidence boosting in rational drug design and indication expansion by leveraging disease association. Inferring potential therapeutic indications (e.g., drug repositioning), for either novel or approved drugs, has become a key approach in drug development. Recently, a number of computational methods have been developed to predict drug indications. There are four typical computational strategies in drug repositioning: (1) predicting drug indications on the basis of the chemical structure of the drug; (2) inferring drug indications from protein targets interaction networks; (3) identifying relationships between drugs based on the similarity of their phenotypic profiles; and (4) integrating multiple properties (e.g., chemical, biological, or phenotypic information) of drugs and diseases to predict drug indications.

SUMMARY OF THE INVENTION

An embodiment of the invention provides a method comprising receiving input in an interface, the input including a list of drugs, drug characteristics of each drug in the list of drugs, and drug-disease associations. Each of the drug-disease associations includes a disease and a drug having a threshold efficacy for treating the disease. A processor predicts whether each drug in the list of drugs meets a threshold efficacy for treating a first disease based on the drug characteristics and the drug-disease associations. The processor also predicts whether each drug in the list of drugs meets a threshold efficacy for treating a second disease based on the drug characteristics and based on whether each drug in the list of drugs meets the threshold efficacy for treating the first disease.

Output is generated based on the predicting of whether the drug meets the threshold efficacy for treating the first disease and the predicting of whether the drug meets the threshold efficacy for treating the second disease. The output includes an identified drug-disease association, an identified disease-disease association, an identified chemical fingerprint for the first disease, and an identified chemical fingerprint for the second disease. The identified drug-disease association includes one or more drugs having a threshold predicted efficacy for treating the first disease and/or the second disease. The identified disease-disease association includes one or more diseases having a threshold level of similarity to the first disease and/or the second disease. The identified chemical fingerprint for the first disease includes a numerical code identifying a known chemical structure having a predicted efficacy for treating the first disease. The identified chemical fingerprint for the second disease includes a numerical code identifying a known chemical structure having a predicted efficacy for treating the second disease.

BRIEF DESCRIPTION OF THE SEVERAL VIEWS OF THE DRAWINGS

The present invention is described with reference to the accompanying drawings. In the drawings, like reference numbers indicate identical or functionally similar elements.

FIG. 3 is a table including key fingerprints for acute pulmonary heart disease.

FIG. 4 is a table including key fingerprints for Schizophrenia.

FIG. 5 is a diagram illustrating a system for drug repositioning according to an embodiment of the invention.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

Figure 1:
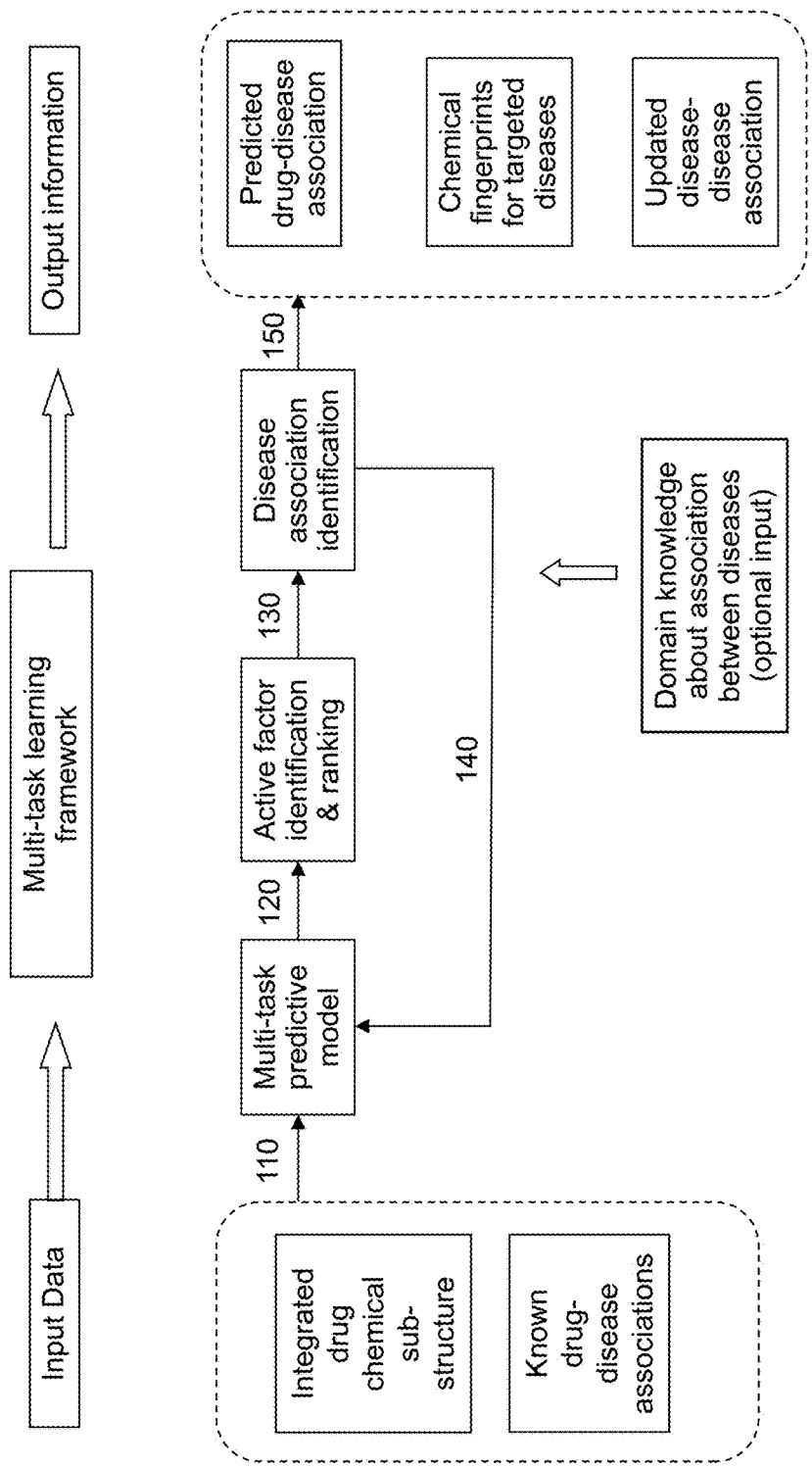
FIG. 1 is a flow diagram illustrating a method for evidence boosting in rational drug design and indication expansion according to an embodiment of the invention.

FIG. 1 is a flow diagram illustrating a method for evidence boosting in rational drug design and indication expansion according to an embodiment of the invention. The method can simultaneously model multiple diseases and leverage disease associations and systematic generation of insights about key chemical fingerprints as well as their relevance for targeted diseases. In at least one embodiment, input data that includes chemical substructures for a list of drugs and known drug-disease associations is input into a multi-task predictive model 110.

For example, the following chemical substructures can be input into the multi-task predictive model 110: >=4 H, >=1 any ring size 3, >=4 unsaturated non-aromatic carbon-only ring size 5, C(~Br)(:C), [As]-C:C-[#1], NC1CC(N)CCC1. In another example, the following known drug-disease associations can be input into the multi-task predictive model 110: Ibuprofen is known to treat rheumatoid arthritis, juvenile rheumatoid arthritis, osteoarthritis, mild to moderate pain, and reduce fever; Atorvastatin is known to treat coronary heart disease, myocardial infarction (MI), stroke, angina, and hypercholesterolemia.

The multi-task predictive model 110 can output active factor identification and ranking data 120, which can be used for disease association identification 130. Disease association identification data can also be input into the multi-task predictive model 140. In addition, domain knowledge about the association between diseases, such as the hierarchical structure of International Classification of Diseases Version 9 (ICD-9), can be input into the multi-task predictive model. In at least one embodiment, output information from the multi-task learning framework (e.g., items 120-140) includes predicted drug-disease association, key chemical fingerprints and their relevance scores for targeted diseases (i.e., a chemical fingerprint's efficacy for treating a particular disease), and/or updated disease association 150.

The method can be feature vector based instead of similarity structure based. Multiple diseases can be simultaneously modeled with a unified model framework, wherein an outlet for incorporating domain knowledge can be provided. Disease association can be extracted based on intermediate results from a predictive model, and key fingerprints of diseases can be identified for future drug discovery.

Figure 2:
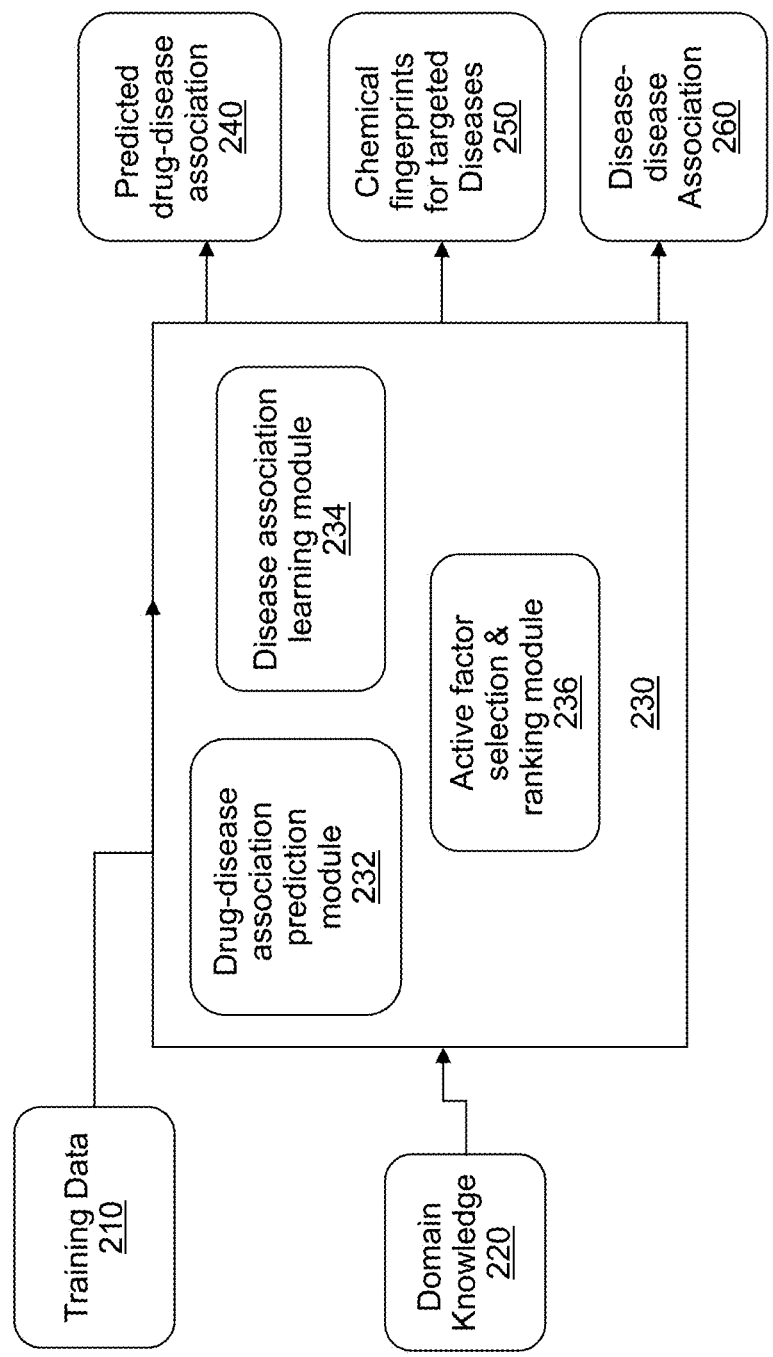
FIG. 2 is a flow diagram illustrating a method for evidence boosting in rational drug design and indication expansion according to another embodiment of the invention.

FIG. 2 is a flow diagram illustrating a method for evidence boosting in rational drug design and indication expansion according to another embodiment of the invention. Training data (also referred to herein as "input data") 210 can include drug characteristics (e.g., chemical structure, chemical-protein interactions, dosage, toxicity, etc.) from multiple sources and integrated known drug-disease pairs from multiple diseases. Input data can also include domain knowledge about disease-disease association and an existing classification of diseases 220.

In at least one embodiment, the training data 210 and domain knowledge 220 is input into a multi-task predictive model 230 that includes a drug-disease association prediction module 232, a disease association learning module 234, and an active factor selection and ranking module 236. The multi-task predictive model 230 can formulate drug repositioning as a binary prediction problem using known drug-disease association as input and output predicted "new" drug-disease pairs. Moreover, the multi-task predictive model 230 can jointly predict multiple diseases under a unified model framework and leverage disease-disease association for achieve improved prediction performance.

Intermediate results from the multi-task predictive model 230 can be fed back into the multi-task predictive model 230 as input to learn disease-disease associations and disease groups. The hierarchical modelling framework can be used to incorporate domain/prior knowledge and facilitate disease similarity learning. As described below, feature selection can be formulated using regularizations and constraints in the multi-task learning framework, and drugs with similar active features can be automatically identified for similar diseases. The multi-task predictive model 230 can output drug-disease associations 240, key chemical fingerprints and their relevance scores for targeted diseases 250, and disease-disease associations 260.

At least one embodiment of the invention provides a computational method for evidence boost in rational drug design and indication expansion by leveraging disease association. The method can construct a computational framework and formulate the task of evidence boosting in drug discovery as a constrained optimization problem. The method can take drug characteristics and known drug-disease association as input, wherein no graph-based metrics are required. Moreover, the method can leverage the relationship between target diseases to achieve enhanced prediction accuracy in drug-disease association discovery.

In at least one embodiment, the system learns and outputs key chemical fingerprints of diseases and outputs relevance scores of the chemical fingerprints for target diseases. A numerical understanding of the chemical structure of a drug can be described by a list binary substructure fingerprint generated by the PubChem fingerprint system. The PubChem fingerprint system can include a total of 881 bits and is composed of 7 sections, such as hierarchic element counts, chemical rings, and simple atom pairs, simple atom nearest neighbors, detailed atom information, and two sections of SMARTS patterns. The learned key chemical fingerprints, together with their relevance scores, can be used to design drugs for specific diseases. For example, FIG. 3 is a table including key fingerprints and their relevance scores for acute pulmonary heart disease; and, FIG. 4 is a table including key fingerprints and their relevance scores for Schizophrenia.

Figure 6:
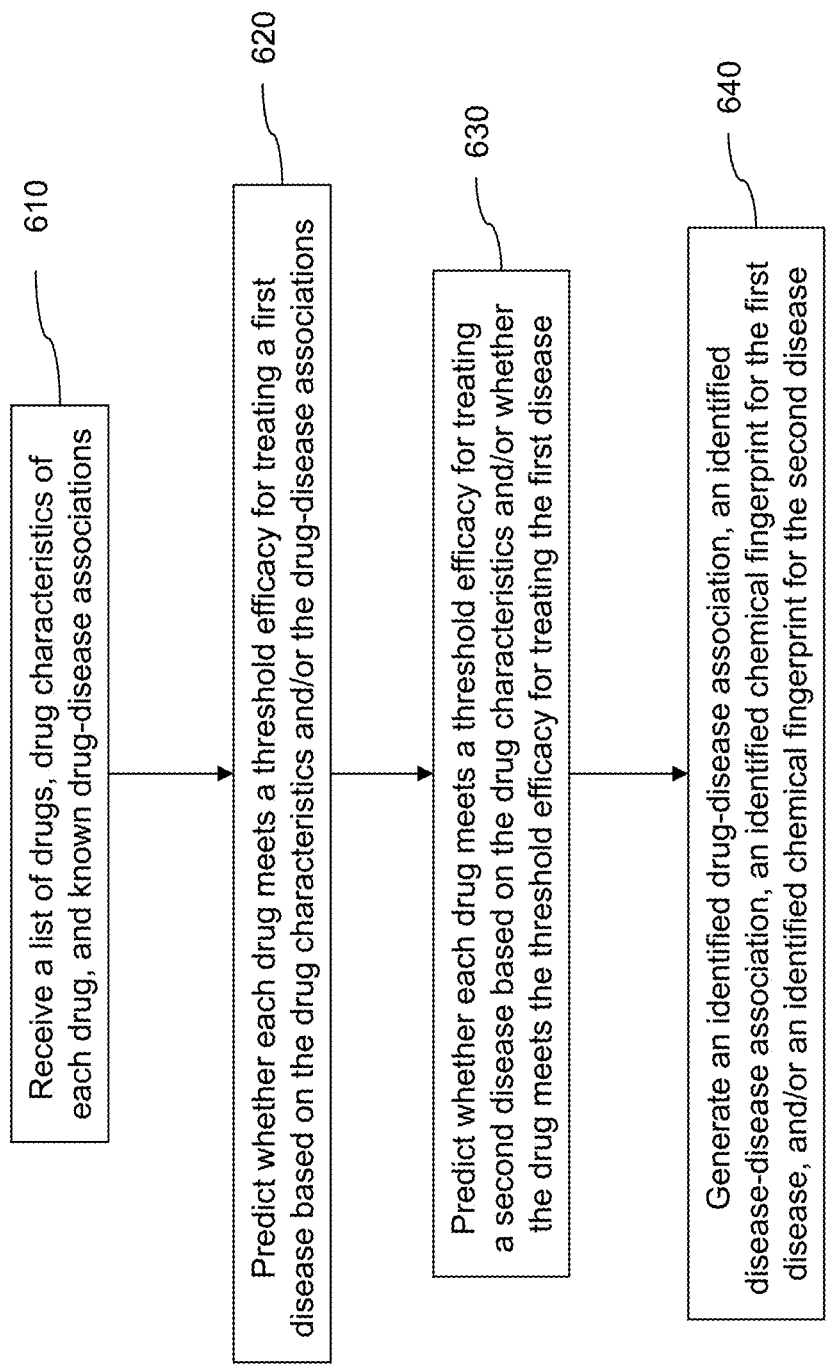
FIG. 6 is a flow diagram illustrating a method for drug repositioning according to an embodiment of the invention.

FIG. 5 is a diagram illustrating a system 500 for drug repositioning according to an embodiment of the invention. FIG. 6 is a flow diagram illustrating a method for drug repositioning according to an embodiment of the invention (e.g., using the system 500). An interface 510 receives input 610, where the input can include a list of drugs, drug characteristics of each drug in the list of drugs, and known drug-disease associations. The drug-disease associations can each include a disease and one or more drugs that have a threshold efficacy for treating the disease. As used herein, the term "interface" can include a computer hardware device, such as, for example, a keyboard, a mouse, a microphone, a touchpad, a touchscreen, a joystick, a controller, a camera, a disk drive, a port, etc.

The drug characteristics can include a chemical structure of a drug and/or a chemical-protein interactome of the drug. The input can further include known disease-disease associations and/or known disease classifications (e.g., classes of diseases such as cancers, diseases of the respiratory system, skin diseases, diseases of the digestive system, and diseases of the musculoskeletal system).

A processor 520 connected to the interface 510 can predict, for each drug in the list of drugs, whether the drug meets a threshold efficacy for treating a first disease (e.g., Alzheimer's disease) based on the drug characteristics and/or the drug-disease associations 620. In another embodiment, the processor predicts whether drugs in the list of drugs meet the threshold efficacy for treating the first disease. As used herein, the terms "drugs in the list of drugs" can include more than one drug, but not all drugs in the list of drugs. Moreover, as used herein, the term "connected" includes operationally connected, logically connected, in communication with, physically or wirelessly connected, engaged, coupled, contacts, linked, affixed, and attached.

Furthermore, the processor 520 can predict, for each drug in the list of drugs, whether the drug meets a threshold efficacy for treating a second disease (e.g., clinical depression) based on the drug characteristics and/or whether the drug meets the threshold efficacy for treating the first disease 630. In another embodiment, the processor predicts whether drugs in the list of drugs meet the threshold efficacy for treating the second disease based on the drug characteristics and/or whether the drugs in the list of drugs meets the threshold efficacy for treating the first disease. In one embodiment of the invention, based on the known association between a drug and the first disease, the predictive model learns a score for each characteristic of a drug, which indicates the importance and/or relevance of the drug characteristics in treating the first disease. The predictive model also learns an optimal efficacy threshold for deciding whether a drug can be a treatment candidate for a disease. The predictive model automatically adjust the learned scores of drug characteristics for a second disease based on intermediate and/or prior knowledge about the association between the first drug and the second drug. The efficacy of the drug for treating the second disease is then decided by a combination of scores from drug characteristics.

In at least one embodiment of the invention, the processor 520 generates output 640 to be displayed on a display 530, where the output includes an identified drug-disease association, an identified disease-disease association, an identified chemical fingerprint for the first disease, and/or an identified chemical fingerprint for the second disease. The output can be generated based on the predictions of whether the drug meets the threshold efficacy for treating the first disease and/or whether the drug meets the threshold efficacy for treating the second disease.

The identified drug-disease association can include one or more drugs that have a threshold predicted efficacy for treating the first disease and/or the second disease. The identified disease-disease association can include one or more diseases that have a threshold level of similarity to the first disease and/or the second disease. The identified chemical fingerprint for the first disease can include a numerical code that identifies a known chemical structure that has a predicted efficacy for treating the first disease. The identified chemical fingerprint for the second disease can include a numerical code that identifies a known chemical structure that has a predicted efficacy for treating the second disease. Such predicted efficacies can be predicted by the processor 520 (e.g., based on the input). The identified drug-disease association can be generated based on the known drug-disease associations, the identified drug-disease association, the identified disease-disease association, the identified chemical fingerprint for the first disease, and/or the identified chemical fingerprint for the second disease.

In at least one embodiment of the invention, rational drug design and indication expansion considers m known diseases and n existing drugs, where $Y \in R^{N \times M}$ denotes the known drug-disease indications. Elements of Y can be encoded by $-1$ or $1$ depending on whether a drug is known to treat a disease. For example, $Y_{nm}=1$ indicates that drug n is known to treat disease m, and $Y_{nm}=-1$ indicates that whether drug n can be used for disease m is unknown. Each drug can be represented by its substructures, where D can denote the number of known substructures. $X \in R^{N \times D}$ can indicate the presence or absence of substructures in the known drugs. $X_{nd}=1$ can indicate that drug n contains substructure d; and, $X_{nd}=0$ can indicates that drug n does not contain substructure d.

The problem of indication expansion and rational drug design can be formulated as the following two questions: (1) for the unknown drug-disease pairs, predict whether the give drug could treat the disease (i.e., model the indication expansion tasks as multiple binary classification problems); and, (2) for each disease, the problem of identifying the effective substructures is formulated as a feature ranking and selection problem.

The problem of jointly predicting drug indications for multiple drugs and multiple diseases can be considered simultaneously. For each risk disease, the binary prediction problem can be formulated into a logistic regression in the following model:

$$\text{logit}(y_{ij} \mid X) = \log \frac{P(y_{ij} = 1 \mid X)}{P(y_{ij} = -1 \mid X)} = x_{(i)} w_j, \quad (1)$$

Logit (.) can denote the logit function, P can denote probability, $x_{(i)}$ can be the presence/absence vector of substructures for the i-th drug, and $w_1$ can be the coefficient vector of disease j. $W=[w_1, \ldots, w_m]$ can be collectively denoted as the coefficient matrix.

In at least one embodiment, the underlying rationale of the multi-task learning method is that similar diseases tend to have similar mechanisms. The relationship between risk targets can be reflected in the hidden structure of the coefficient matrix W. Specifically, if two risk targets (risk i and j) are strongly related, the system can assume that the effects of a feature on the two targets are similar. In other words, their corresponding coefficient vectors ($w_i$ and $w_j$) tend to be similar. This assumption can be incorporated into the model by a hierarchical structure. In particular, a prior distribution can be added on W in the following model:

$$W \sim MVN(0, \epsilon^2 I, \Omega). \quad (2)$$

MVN can represent the Matrix Variate Normal distribution, 0 can represent the location of W; $\epsilon^2 I$ can be the covariance matrix between rows of W, which can reflect the covariances between coefficients of different features. The third term $\Omega$ can be the column-wise covariance of W, which can characterize the target relatedness. The system can learn both the coefficient matrix W and the target relatedness covariance matrix simultaneously.

The system can assume that similar diseases (e.g. diseases classified in the same group in the ICD-9 coding system) are highly correlated. While a data-driven approach can aim at learning disease relatedness from data, properly incorporating domain knowledge can be of great help in improving the learned disease relatedness. In order to blend domain knowledge into a data-driven approach, an additional layer of hierarchical model can be added by imposing a prior distribution on $\Omega$ in the following model:

$$\Omega \sim IW(\alpha \Omega_0, v). \quad (3)$$

IW can denote the Inverse-Wishart distribution, which can be the conjugate prior of Multivariate Normal distribution; and a and v can be tuning parameters. $\Omega_0$ can be a predefined covariance matrix that contains all domain knowledge about disease relatedness. In at least one embodiment, a positive element in $\Omega_0$ indicates that two diseases are positively correlated, a negative element indicates that two diseases are negatively correlated, and a zero element indicates that two diseases are not correlated.

The feature selection problem can be naturally coupled with the problems of drug indication expansion and learning disease relatedness. First, different diseases could have different sets of key chemical fingerprints. In at least one embodiment, all candidate features are included for all targets in the framework. Therefore, the first goal of feature selection can be to identify a subset of "active" features for each disease. Second, diseases may form groups due to their underlying mechanisms. A group of diseases may be correlated with each other while not correlated with another group of diseases. The second goal of feature selection can be to identify the pairs or groups of diseases that are correlated with each other. The two goals can indicate that sparsity is desired for both W and $\Omega$.

Regularization methods can be used in feature selection to obtain parsimonious solutions. In particular, the Least Absolute Shrinkage and Selection Operator (Lasso) model, which uses the $l_1$ regularizer can be used in feature selection. The $l_1$ regularizer can be used on both W and $\Omega$ for feature and covariance selections.

Combining the regularizers and above models, the following objective function can be solved:

$$\min_{W,\Omega} \sum_{i,j} \log(1 + \exp(-y_{ij}x_{(i)}w_j)) + \quad (4)$$

$$tr\left(\left(\frac{\lambda_1}{2}W^TW + \alpha\Omega_0\right)\Omega^{-1}\right) + \frac{\lambda_2}{2}\log\det(\Omega) + \gamma_1|W|_1 + \gamma_2|\Omega|_1$$

In at least one embodiment, tr (.) denotes the trace of a matrix, log det (.) denotes the logarithm of determinant, $1.1_1$ denotes the $l_1$ regularizer, and $\lambda_1$, $\lambda_2$, $\alpha$, $y_1$ and $y_2$ are non-negative tuning parameters. The system can deal with binary targets and perform drug indication expansion, disease relatedness exploration, and feature selection simultaneously. By introducing $\Omega_0$, the system can provide a way to blend data-driven and knowledge-driven approaches to learn disease relatedness.

In at least one embodiment, directly solving the optimization problem (4) is complicated since the log det ($\Omega$) term is non-convex with respect to $\Omega$. The following optimization problem can be solved:

$$\min_{W,\Omega} \sum_{i,j} \log(1 + \exp(-y_{ij}x_{(i)}w_j)) + \quad (5)$$

$$tr\left(\left(\frac{\lambda_1}{2}W^TW + \alpha\Omega_0\right)\Omega^{-1}\right) + \gamma_1|W|_1 + \gamma_2|\Omega|_1$$

s.t. $\Omega \succeq 0$ $tr(\Omega) = 1$

A Block Coordinate Descent (BCD) procedure can be used to solve the problem. Starting from an initial point ($W^{(0)}$, $\Omega^{(0)}$), at the t-th iteration, ($W^{(t)}$, $\Omega^{(t)}$) can be updated. Specifically, the system can fix $\Omega = \Omega^{(t-1)}$ and update W. Additionally, the system can fix $W = W^{(t)}$ and update $\Omega$. When $\Omega$ is fixed, a Proximal Gradient Descent algorithm can be used to update W. The following function can be defined:

$$f_w(W) = \sum_{i,j} \log(1 + \exp(-y_{ij}x_{(i)}w_j)) + \frac{\lambda_1}{2}tr(W^TW\Omega^{-1}). \quad (6)$$

$h_w(W) = \nabla_w f_w(W)$ can denote the gradient of $f_w$ with respect to W, $V = W^{(t-1)} - (1/n)h_w(W^{(t-1)})$ $y = y1/n$, and n a pre-determined step size. $G(v_{ij}, y)$ can be the element-wise shrinkage operator defined as follows:

$$\mathcal{G}(v_{ij}, \gamma) = \begin{cases} v_{ij} - \gamma & \text{if } v_{ij} > \gamma, \\ v_{ij} + \gamma & \text{if } v_{ij} < -\gamma, \\ 0 & \text{otherwise.} \end{cases} \quad (7)$$

At each iteration, W can be updated using an element-wise shrinkage operator. When W is fixed, $\Omega$ can be updated. In at least one embodiment, $S = (W^{(t)})^T W^{(t)} + \alpha^*\Omega_0$ where $\alpha^* = 2\alpha/\lambda_1$, and $U = S/tr(S)$. At each iteration, $\Omega$ can be updated by element-wise applying the thresholding operator $G(u_{ij}, y_2)$ to all non-diagonal elements of U.

At least one embodiment of the invention discovers that diseases are related to each other and learns multiple related tasks simultaneously improves the prediction performance of drug repositioning. A multi-task learning (MTL) framework is provided to generate drug repositioning hypotheses and compare it with single-task learning (STL) strategy.

At least one embodiment of the invention collects 1255 drugs from DrugBank, where each drug is represented by an 881-dimensional binary profile whose elements encode for the presence or absence of each PubChem substructure by 1 or 0, respectively. The known uses of these drugs can be collected from a MEDI database. Indications in MEDI can be coded as ICD9 codes. ICD9 codes can be grouped based on their first 3 digits to avoid trivial predictions (i.e., repurpose a drug from a disease to very similar diseases). Non-disease conditions and rare diseases can be excluded, which can result in 100 ICD9 groups as diseases in the drug repositioning process. Between the 1255 drugs and 100 diseases, there can be 3430 distinct drug-disease interactions in the dataset.

The drug repositioning task can be modeled as a binary classification problem. A classifier can be constructed for predicting whether a given drug can treat a particular disease or not, and this process can be repeated for all 100 diseases. In the scenario of STL, such 100 tasks can be solved independently, ignoring the task relatedness. However, the tasks of predicting disease indications of drugs can be related (as a disease might associate with other diseases in real life). In MTL, these related tasks can be learnt simultaneously by extracting and utilizing appropriate shared information across tasks.

Figure 7:
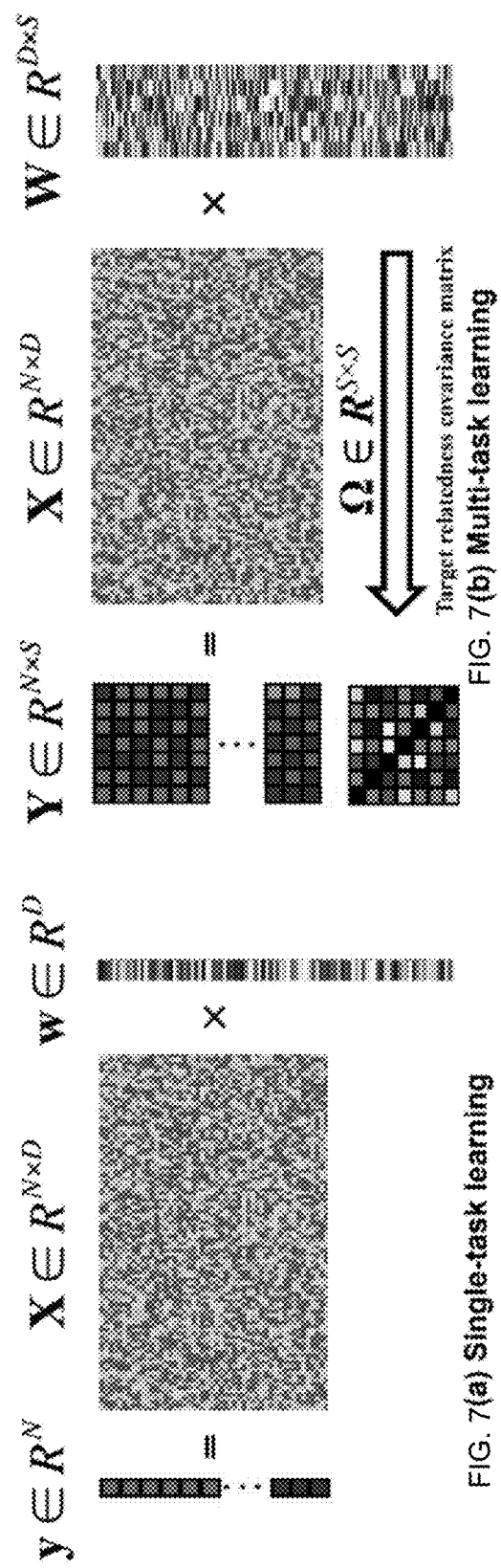
FIG. 7A is a diagram illustrating single task learning according to an embodiment of the invention.
FIG. 7B is a diagram illustrating multi-task learning according to an embodiment of the invention.

FIG. 7 illustrates the difference between STL and MTL according to an embodiment of the invention. In STL, each task can be considered to be independent and learnt independently. $y \in R^N$ can be a vector indicating whether each drug in a drug list is known to treat a disease, and $X \in R^{N \times D}$ can denote the presence of substructures for each drug in the list of drugs. $W \in R^D$ can denote the coefficients of substructures for treating the disease. Each disease (e.g. task) is modeled individually and disease association is not utilized. In MTL, multiple tasks can be learnt simultaneously, by utilizing task relatedness. $Y \in R^{N \times S}$ in panel (b) of FIG. 7 can be an indicating matrix. The (i,j)-th element of Y (i-th row and j-th column) indicate whether drug i is known to treat disease j. $X \in R^{N \times D}$ has the same meaning as in panel (a). $W \in R^{D \times S}$ can be the the coefficient matrix, column j of W is the coefficients of substructures for treating disease j. $\Omega$ can be task covariance matrix of W indicating the disease relatedness. The MTL framework leverages disease associations and diseases are simultaneous modeled together.

Logistic regression can be used as the base classifier to compare STL and MTL. A multi-task relationship learning model can be extended to deal with binary targets and can be applied to the drug repositioning. Imposing prior knowledge to target relatedness can improve the performance of MTL predictions, where the prior knowledge can come from the hierarchical structure of ICD9 codes (i.e., disease areas and grouping information of the targets). Three drug repositioning methods can be considered: (1) STL; (2) MTL without prior; (3) and MTL with prior knowledge. A 10-fold cross validation scheme can be used to evaluate the performance of all methods.

Figure 8:
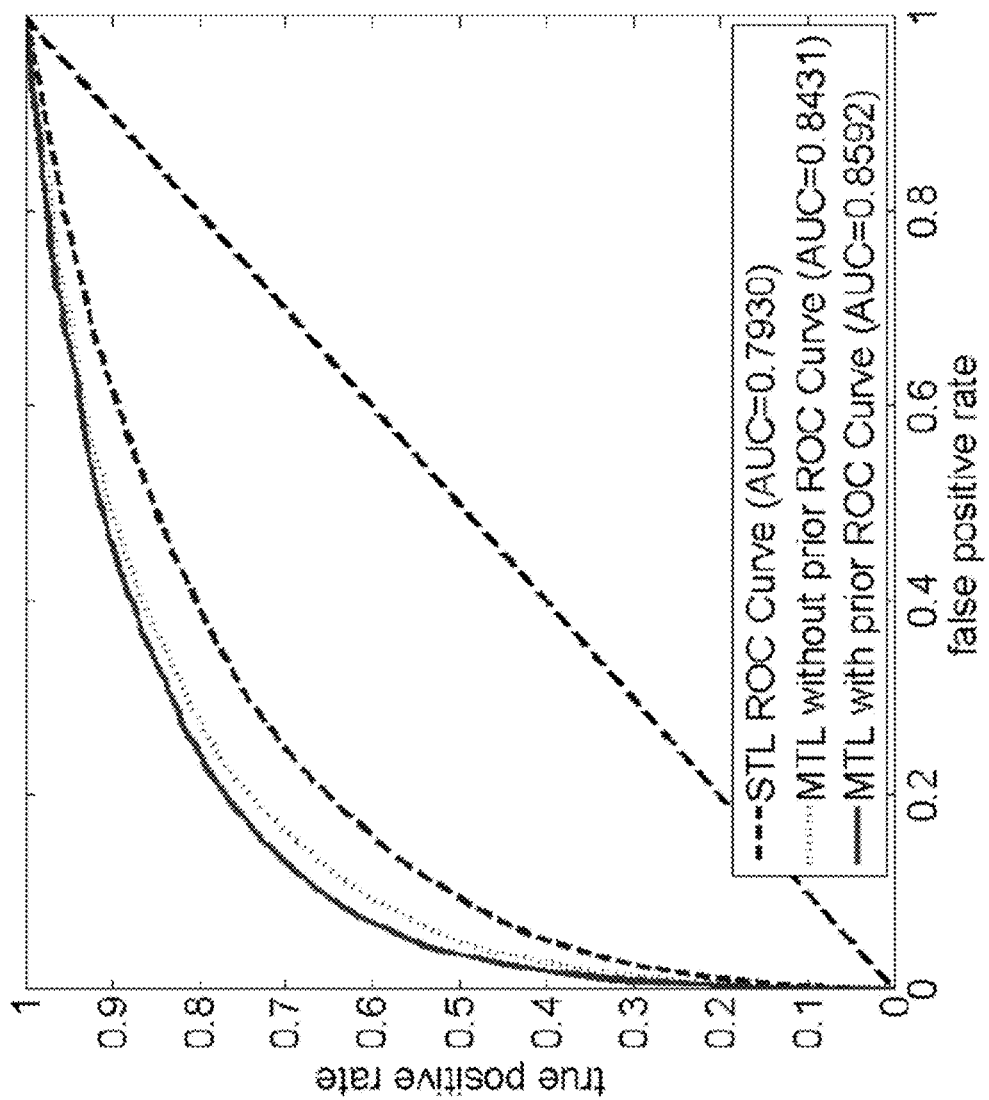
FIG. 8 is a graph illustrating the ROC curves of three methods according to an embodiment of the invention.

FIG. 8 is a graph illustrating the ROC curves of the three methods according to an embodiment of the invention, where MTL without prior knowledge and MTL with prior knowledge obtained AUC scores of 0.8431 and 0.8592, respectively, which are significantly higher than that of STL (0.7930). Learning multiple related tasks simultaneously can effectively increase the training sample (i.e., known drug-disease interactions) size for each task and improve the prediction performance. FIG. 8 also shows that incorporating prior knowledge from an ICD9 hierarchical structure can improve the performance of MTL predictions.

Figure 9:
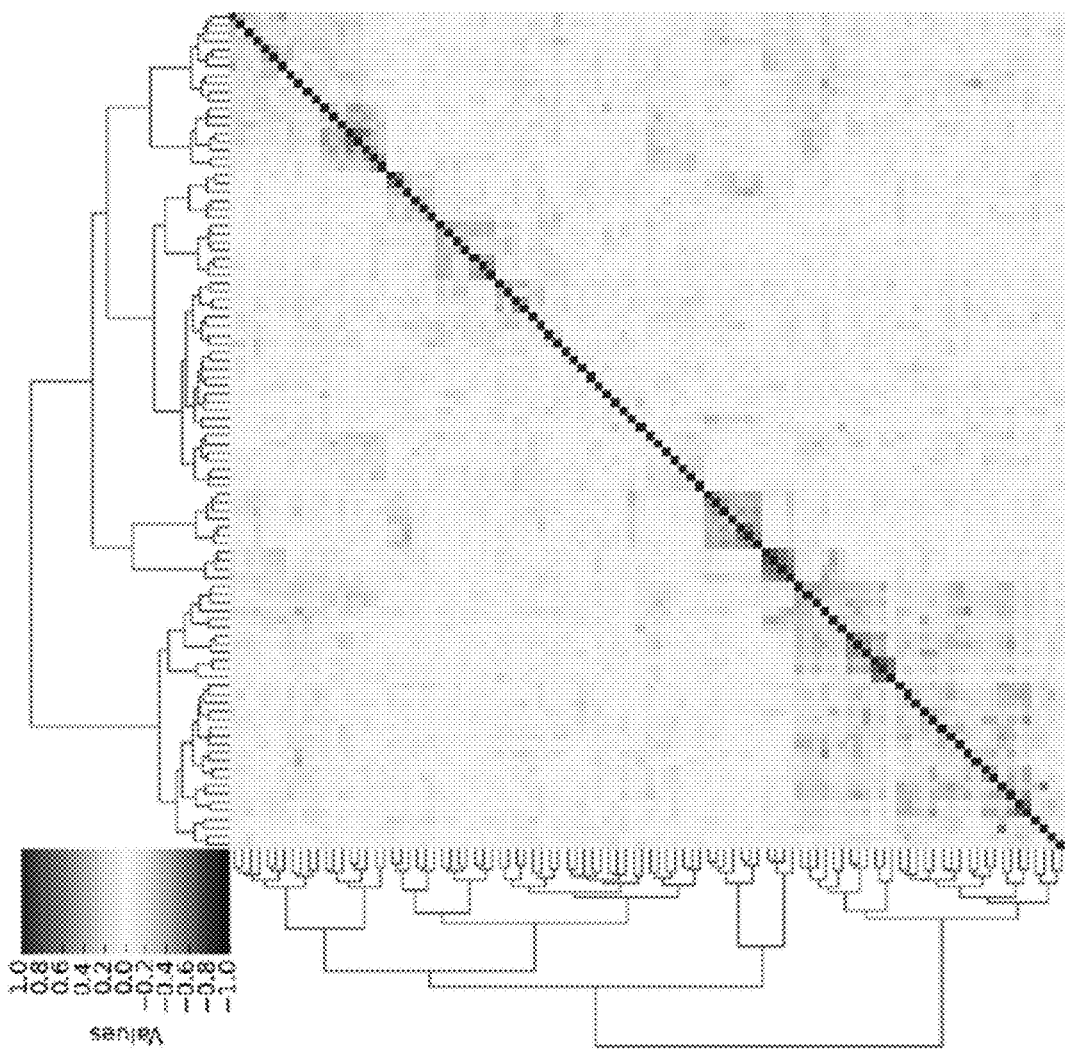
FIG. 9 is a heatmap of learned target relatedness from multi-task learning with prior knowledge according to an embodiment of the invention.

MTLs can also learn target relatedness (i.e., disease associations) during the predictions. FIG. 9 is a heatmap of learned target relatedness from MTL with prior knowledge according to an embodiment of the invention. In the heatmap, a high value between two tasks can indicate the two diseases are highly correlated during the predictions. For example, ICD9 group 401 (hypertension) is highly correlated with ICD9 group 299 (autism) by MTL with prior knowledge, which is in agreement with clinical trials. The learned target relatedness from MTL could provide additional insights for downstream investigations including clinical trials.

The MTL framework provides a feature-vector based multi-task learning method for drug repositioning hypothesis generation. Learning multiple related tasks simultaneously can be effective in achieving improved performance. Furthermore, learned target relatedness from MTL could help to reveal MoA of drug repositioning hypotheses.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 10:
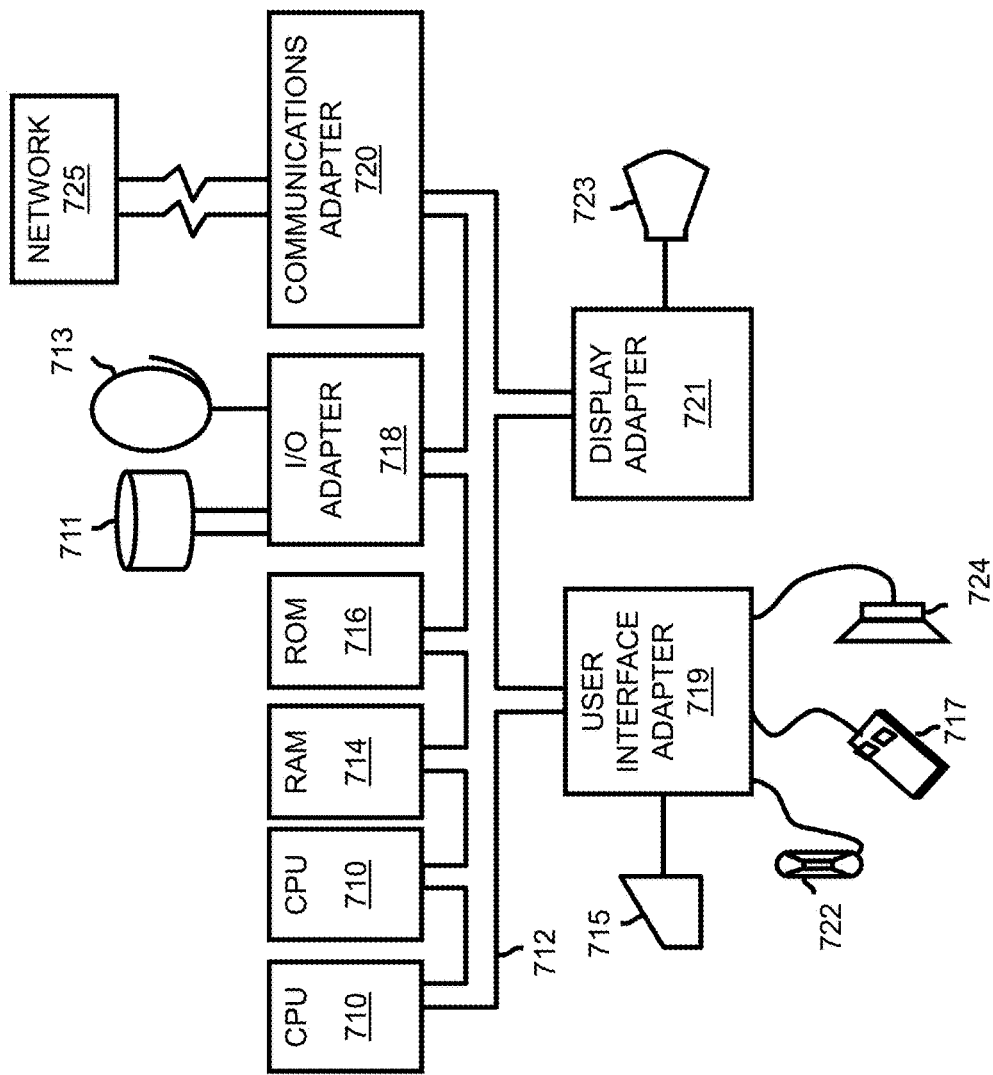
FIG. 10 is a diagram illustrating a computer program product according to an embodiment of the invention.

Referring now to FIG. 10, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 710. The CPUs 710 are interconnected with system bus 712 to various devices such as a random access memory (RAM) 714, read-only memory (ROM) 716, and an input/output (I/O) adapter 718. The I/O adapter 718 can connect to peripheral devices, such as disk units 711 and tape drives 713, or other program storage devices that are readable by the system. The system can read the inventive instructions on the program storage devices and follow these instructions to execute the methodology of at least one embodiment of the invention. The system further includes a user interface adapter 719 that connects a keyboard 715, mouse 717, speaker 724, microphone 722, and/or other user interface devices such as a touch screen device (not shown) to the bus 712 to gather user input. Additionally, a communication adapter 720 connects the bus 712 to a data processing network 725, and a display adapter 721 connects the bus 712 to a display device 723 which may be embodied as an output device such as a monitor, printer, or transmitter, for example.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.'

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 11:
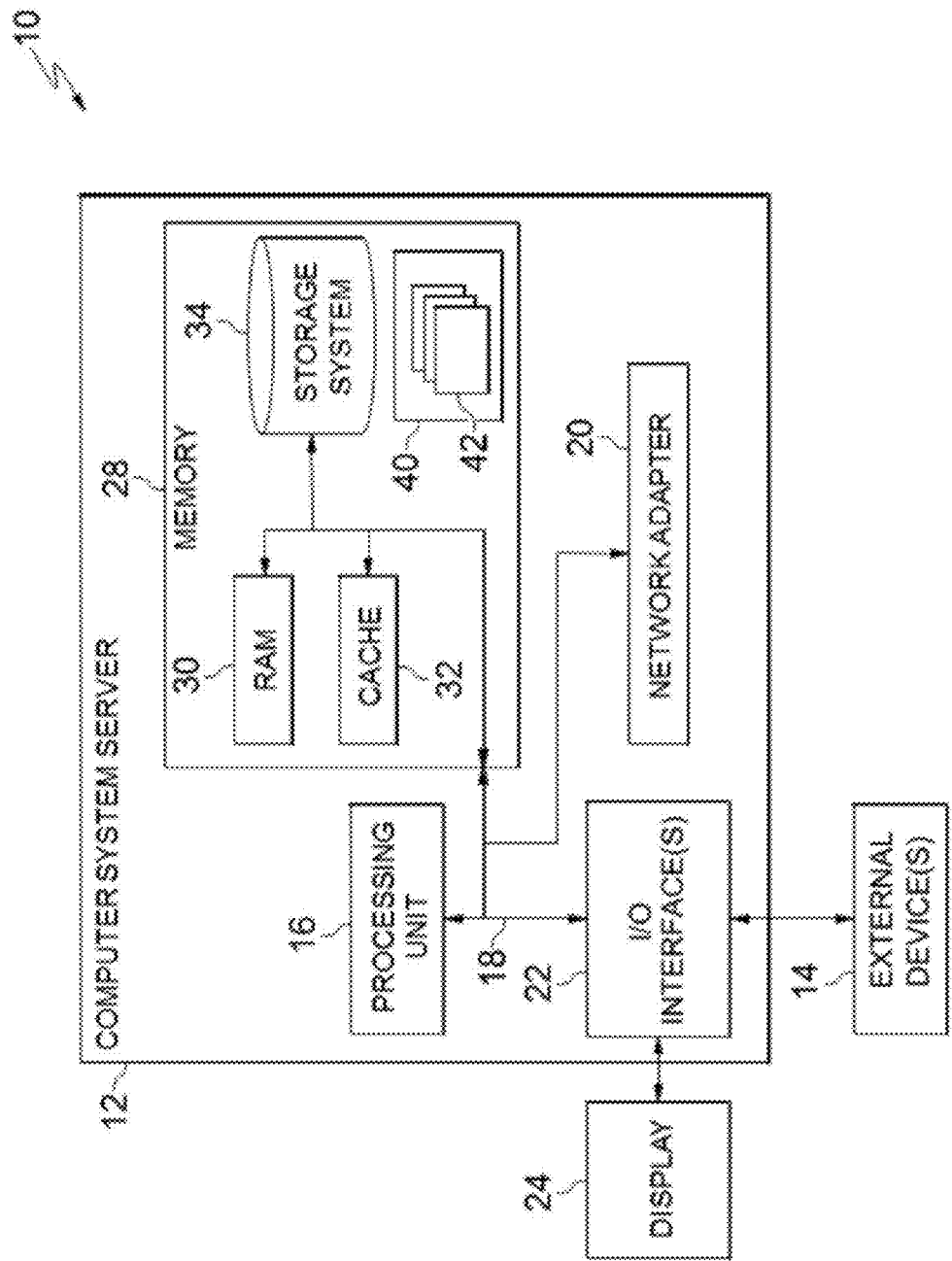
FIG. 11 depicts a cloud computing node according to an embodiment of the present invention.

Referring now to FIG. 11, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer systemexecutable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 12:
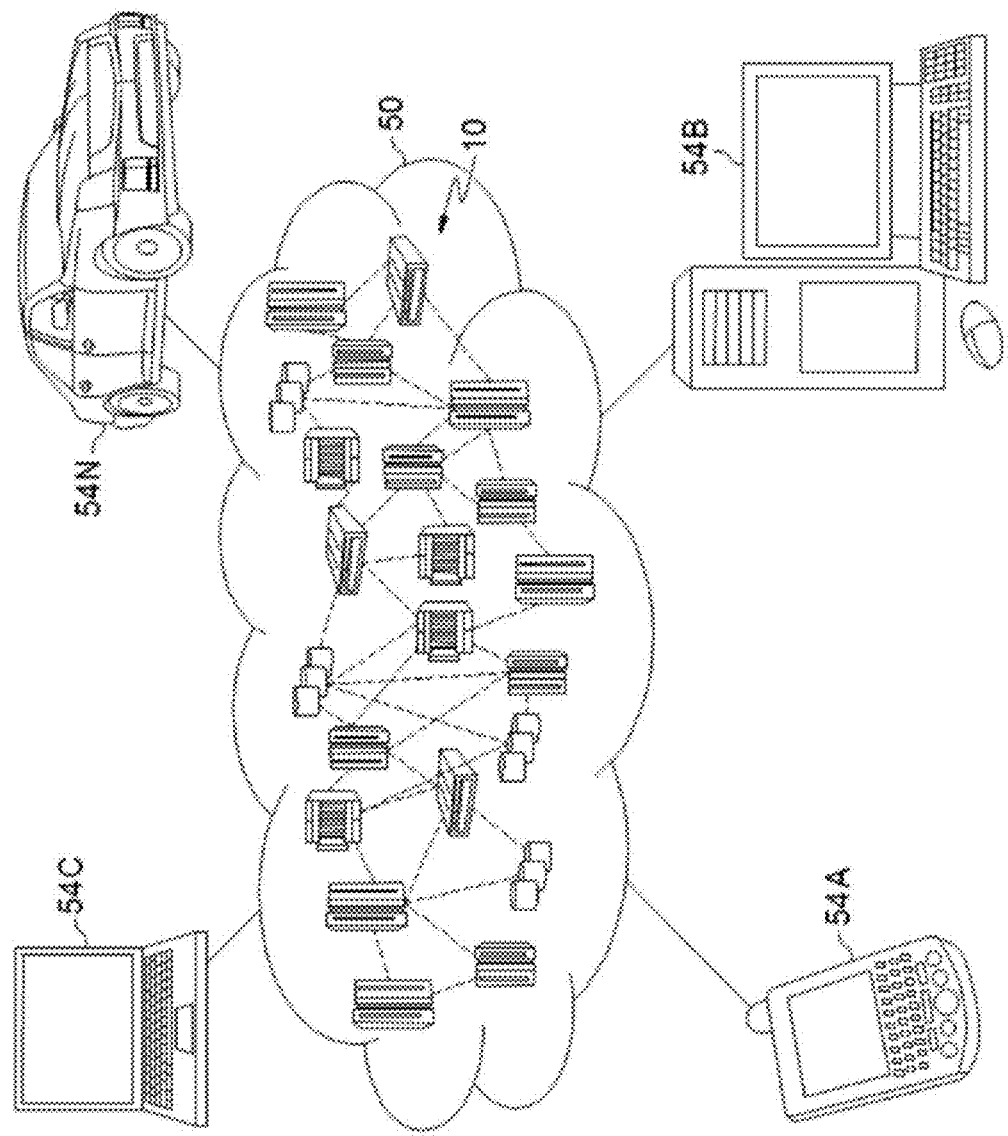
FIG. 12 depicts a cloud computing environment according to an embodiment of the present invention.

Referring now to FIG. 12, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 12 are intended to be illustrative only and that computing nodes 10 and cloud computing environment 50 can communicate with any type of computerized device over any type of network and/or network addressable connection (e.g., using a web browser).

Figure 13:
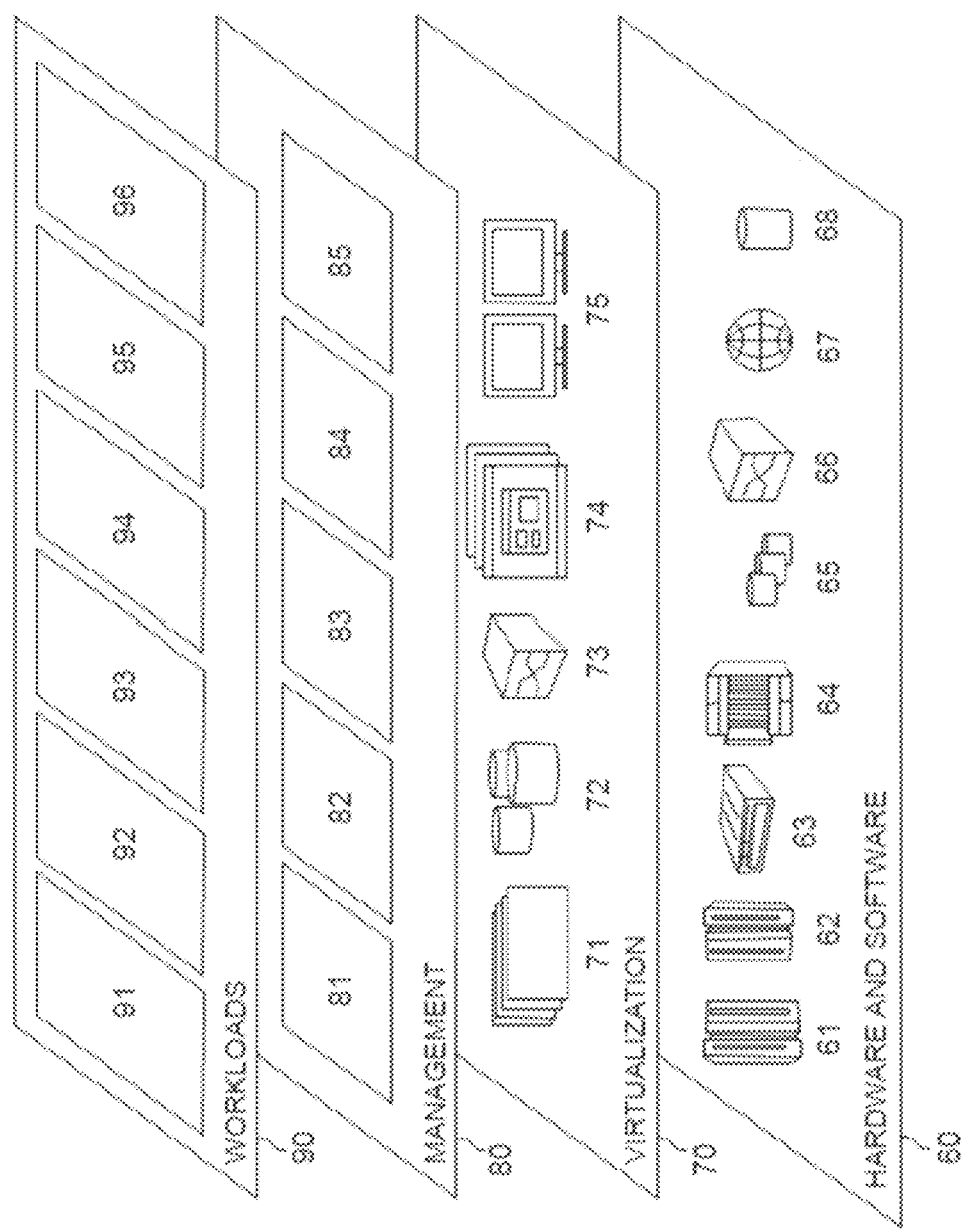
FIG. 13 depicts abstraction model layers according to an embodiment of the present invention.

Referring now to FIG. 13, a set of functional abstraction layers provided by cloud computing environment 50 (FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and evidence boosting in rational drug design and indication expansion 96.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   receiving input in an interface, the input including a list of drugs, drug characteristics of each drug in the list of drugs, and drug-disease associations, each of the drug-disease associations including a disease and a drug having a threshold efficacy for treating the disease;
   predicting, with a processor, whether each drug in the list of drugs meets a threshold efficacy for treating a first disease based on the drug characteristics and the drug-disease associations;
   predicting, with the processor, whether each drug in the list of drugs meets a threshold efficacy for treating a second disease based on the drug characteristics and said predicting whether each drug in the list of drugs meets the threshold efficacy for treating the first disease; and
   generating output based on said predicting whether the drug meets the threshold efficacy for treating the first disease and said predicting whether the drug meets the threshold efficacy for treating the second disease, the output including:
   an identified drug-disease association,
   an identified disease-disease association,
   an identified chemical fingerprint for the first disease, and
   an identified chemical fingerprint for the second disease,
   the identified drug-disease association including at least one drug having a threshold predicted efficacy for treating at least one of the first disease and the second disease;
   the identified disease-disease association including at least one disease having a threshold level of similarity to at least one of the first disease and the second disease;
   the identified chemical fingerprint for the first disease including a numerical code identifying a known chemical structure having a predicted efficacy for treating the first disease; and
   the identified chemical fingerprint for the second disease including a numerical code identifying a known chemical structure having a predicted efficacy for treating the second disease.

2. The method according to claim 1, wherein the drug characteristics include a chemical structure of a drug.

3. The method according to claim 1, wherein the drug characteristics include a chemical-protein interactome of the drug.

4. The method according to claim 1, wherein the input further includes known disease-disease associations.

5. The method according to claim 1, wherein the input further includes known disease classifications.

6. The method according to claim 1, wherein said generating of the output includes generating the identified drug-disease association based on the drug-disease associations.

7. The method according to claim 1, wherein said generating of the output includes generating the identified drug-disease association based on the identified drug-disease association.

8. The method according to claim 1, wherein said generating of the output includes generating the identified drug-disease association based on the identified disease-disease association.

9. The method according to claim 1, wherein said generating of the output includes generating the identified drug-disease association based on the identified chemical fingerprint for the first disease.

10. The method according to claim 1, wherein said generating of the output includes generating the identified drug-disease association based on the identified chemical fingerprint for the second disease.

11. A method comprising:
receiving input in an interface, the input including a list of drugs, drug characteristics of drugs in the list of drugs, and drug-disease associations, each of the drug-disease associations including a disease and a drug having a threshold efficacy for treating the disease;
predicting, with a processor, whether drugs in the list of drugs meet a threshold efficacy for treating a first disease based on at least one of the drug characteristics and the drug-disease associations;
predicting, with the processor, whether the drugs in the list of drugs meet a threshold efficacy for treating a second disease based on said predicting whether the drugs in the list of drugs meet the threshold efficacy for treating the first disease; and
generating output including at least one of:
an identified drug-disease association,
an identified disease-disease association,
an identified chemical fingerprint for the first disease, and
an identified chemical fingerprint for the second disease,
the identified drug-disease association including at least one drug having a threshold predicted efficacy for treating at least one of the first disease and the second disease;
the identified disease-disease association including at least one disease having a threshold level of similarity to at least one of the first disease and the second disease;
the identified chemical fingerprint for the first disease including a numerical code identifying a known chemical structure having a predicted efficacy for treating the first disease; and
the identified chemical fingerprint for the second disease including a numerical code identifying a known chemical structure having a predicted efficacy for treating the second disease.

12. The method according to claim 11, wherein the drug characteristics include a chemical structure of a drug.

13. The method according to claim 11, wherein the drug characteristics include a chemical-protein interactome of the drug.

14. The method according to claim 11, wherein the input further includes at least one of known disease-disease associations and known disease classifications.

15. The method according to claim 11, wherein said generating of the output includes generating the identified drug-disease association based on the drug-disease associations.

16. The method according to claim 11, wherein said generating of the output includes generating the identified drug-disease association based on the identified drug-disease association.

17. The method according to claim 11, wherein said generating of the output includes generating the identified drug-disease association based on the identified disease-disease association.

18. The method according to claim 11, wherein said generating of the output includes generating the identified drug-disease association based on the identified chemical fingerprint for the first disease.

19. The method according to claim 11, wherein said generating of the output includes generating the identified drug-disease association based on the identified chemical fingerprint for the second disease.

20. A computer program product comprising:
a non-transitory computer readable storage medium having stored thereon:
first program instructions executable by a device to cause the device to receive input, the input including a list of drugs, drug characteristics of each drug in the list of drugs, and drug-disease associations, each of the drug-disease associations including a disease and a drug having a threshold efficacy for treating the disease;
second program instructions executable by the device to cause the device to, for each drug in the list of drugs, predict whether the drug meets a threshold efficacy for treating a first disease based on at least one of the drug characteristics and the drug-disease associations;
third program instructions executable by the device to cause the device to, for each drug in the list of drugs, predict whether the drug meets a threshold efficacy for treating a second disease based on the predicting of whether the drug meets the threshold efficacy for treating the first disease; and
fourth program instructions executable by the device to cause the device to generate output including at least one of:
an identified drug-disease association,
an identified disease-disease association,
an identified chemical fingerprint for the first disease, and
an identified chemical fingerprint for the second disease,
the identified drug-disease association including at least one drug having a threshold predicted efficacy for treating at least one of the first disease and the second disease;
the identified disease-disease association including at least one disease having a threshold level of similarity to at least one of the first disease and the second disease;
the identified chemical fingerprint for the first disease including a numerical code identifying a known chemical structure having a predicted efficacy for treating the first disease; and
the identified chemical fingerprint for the second disease including a numerical code identifying a known chemical structure having a predicted efficacy for treating the second disease.

* * * * *